(12) United States Patent
Sotomayor et al.

(10) Patent No.: US 7,404,963 B2
(45) Date of Patent: Jul. 29, 2008

(54) FLAGELLIN-BASED ADJUVANTS AND VACCINES

(75) Inventors: Eduardo M. Sotomayor, Tampa, FL (US); Ildefonso Suarez, Tampa, FL (US)

(73) Assignee: The University of South Florida, Tampa, FL (US)

( * ) Notice: Subject to any disclaimer, the term of this patent is extended or adjusted under 35 U.S.C. 154(b) by 0 days.

(21) Appl. No.: 11/243,450

(22) Filed: Oct. 3, 2005

(65) Prior Publication Data

US 2006/0088555 A1   Apr. 27, 2006

Related U.S. Application Data

(60) Provisional application No. 60/615,550, filed on Oct. 1, 2004.

(51) Int. Cl.
  *A61K 39/00* (2006.01)
  *A61K 51/00* (2006.01)
  *A61M 36/14* (2006.01)

(52) U.S. Cl. .................. 424/277.1; 424/1.11; 424/1.65

(58) Field of Classification Search ........................ None
  See application file for complete search history.

(56) References Cited

U.S. PATENT DOCUMENTS

| 6,130,082 | A | 10/2000 | Majarian et al. |
| 2003/0044429 | A1 | 3/2003 | Aderem et al. |
| 2003/0170756 | A1 | 9/2003 | Berd |
| 2005/0257280 | A1 | 11/2005 | Akira |
| 2006/0002941 | A1 | 1/2006 | Mahairas |

OTHER PUBLICATIONS

Sbrogio-Almeida, M.E., Mosca, T., Massis, L.M., Abrahamsohn, I.A., and Ferreira, L.C.S. Host and bacterial factors affecting induction of immune responses to flagellin expressed by attenuated *Salmonella* vaccine strains. 2004. Infection and Immunity, vol. 72 No. 5, pp. 2546-2555.*
Sfondrini, L., Rossini, A., Besusso, D., Merlo, A., Tagliabue, E., Menard, S., and Balsari, A. Antitumor activity of the TLR-5 ligand flagellin in mouse models of cancer. 2006. Journal of Immunology, vol. 176. pp. 6624-6630.*
Pawelek, J.M., Low, K.B., and Bermudes, D. Tumor-targeted *Salmonella* as a novel anticancer vector. 1997. Cancer Research, vol. 57, pp. 4537-4544.*
Mitchell, M.S. Cancer vaccines, a critical review—Part I. 2001. Current Opinion in Investigational Drugs. vol. 3 No. 1, pp. 140-149.*
Margulis, L. Undulipodia, flagella and cilia. Biosystems, 1980, vol. 12, pp. 105-108 (abstract only).*
Berg, J.M., Tymoczko, J.L., Stryer, L., and Clarke, N.D., eds. Biochemistry. 5th edition, W.H. Freeman and Company, 2002. pp. 34-35 and 967.*
Borrello, I., et al. (1999). A universal granulocyte-macrophage colony-stimulating factor-producing bystander cell line for use in the formulation of autologous tumor cell-based vaccines. Hum Gene Ther. 10(12):1983-1991.

Bretscher, P., and Cohn, M. (1970). A theory of self-nonself discrimination. Science. 169(950):1042-1049.
Cheng, F., et al. (2003). A critical role for Stat3 signaling in immune tolerance. Immunity. 19(3):425-436.
Ibrahim, G.F., et al. (1985). Method for the isolation of highly purified *Salmonella flagellins*. J Clin Microbiol. 22(6):1040-1044.
Jenkins, M.K., and Schwartz, R.H. (1987). Antigen presentation by chemically modified splenocytes induces antigen-specific T cell unresponsiveness in vitro and in vivo. J Exp Med. 165(2):302-319.
Levitsky, H.I., et al. (1994). In vivo priming of two distinct antitumor effector populations: the role of MHC class I expression. J Exp Med. 179(4):1215-1224.
McSorley, S.J., et al. (2002). Bacterial flagellin is an effective adjuvant for CD4+ T cells in vivo. J Immunol. 169(7):3914-3919.
Mizel, S.B., et al. (2003). Identification of a sequence in human toll-like receptor 5 required for the binding of gram-negative flagellin. J Biol Chem. 278(26):23624-23629.
Murthy, K.G., et al. (2004). Identification of conserved domains in *Salmonella muenchen* flagellin that are essential for its ability to activate TLR5 and to induce an inflammatory response in vitro. J Biol Chem. 279(7):5667-5675.
Smith, K.D., et al. (2003). Toll-like receptor 5 recognizes a conserved site on flagellin required for protofilament formation and bacterial motility. Nat Immunol. 4(12):1247-1253.
Didierlaurent, A., et al. (2004). Flagellin promotes myeloid differentiation factor 88-dependent development of Th2-type response. J Immunol. 172(11):6922-6930.
Hayashi, F., et al. (2001). The innate immune response to bacterial flagellin is mediated by toll-like receptor 5. Nature. 410(6832):1099-1103.
Eaves-Pyles, et al., "*Salmonella* Flagellin-Dependent Proinflammatory Responses are Localized to the Conserved Amino and Carobxyl Regions of the Protein," *The Journal of Immunology*, 167: 7009-7016 (2001).

* cited by examiner

*Primary Examiner*—Larry R. Helms
*Assistant Examiner*—Anne M Gussow
(74) *Attorney, Agent, or Firm*—Fish & Richardson P.C.

(57) ABSTRACT

The present invention provides adjuvants, vaccines and related methods that are useful in eliciting immune responses, particularly immune responses against tumor antigens. We discovered that flagellin is capable of inhibiting tolerance when it is administered in conjunction with a tolerogenic antigen. This effect is likely mediated by the ability of flagellin to induce IL-12 while keeping IL-10 levels low. Furthermore, flagellin can be provided in an extended-releasing manner by using a flagellin-expressing cell. Preferably, the flagellin-expressing cell is treated such that it is no longer capable of replicating, yet retaining the ability to express flagellin, such as by lethal irradiation.

21 Claims, 12 Drawing Sheets

A

B

A

WB anti flagellin

B

FLAGELLIN-BASED ADJUVANTS AND VACCINES

CROSS-REFERENCE TO RELATED APPLICATIONS

This application claims the benefit of U.S. Provisional Application Ser. No. 60/615,550, filed Oct. 1, 2004, the entire content of which is incorporated herein by reference.

FIELD OF INVENTION

This invention relates to adjuvants and vaccines, and uses thereof.

BACKGROUND

The discovery of tumor specific antigens (neoantigens) that arise during tumor development inspired Burnet's immune surveillance theory. This theory states that the immune system is able to recognize and eliminate newly developing tumors based on the presence of neoantigens. However, since then many experiments have shown that immunocompromised individuals do not develop more malignancies than normal immunocompetent individuals, thus contradicting the idea that the immune system plays a protective role against the development of cancer. Therefore, it appears that tumors and their specific antigens do not provoke any immune response.

This phenomenon can be explained by the "two signal model of lymphocyte activation" of Brestcher and Cohn (Brestscher, P. and M. Cohn, A theory of self-nonself discrimination, Science (1970) 169(950):1042). This model states that for full activation of a T cell, two signals must be provided. Signal one comes from the recognition of a specific antigen through engagement of the T cell receptor, and signal two is provided by costimulatory molecules present on the antigen-presenting cell (APC). In the absence of costimulation, the T cell will not elicit an immune response against the antigen. Rather, it will assume a state known as anergy (Jenkins, M. K., and Schwartz R. H., Antigen presentation by chemically modified splenocytes induces antigen-specific T cell unresponsiveness in vitro and in vivo, J Exp Med (1987) 165(2): p. 302-319), which will be maintained even if the antigen is provided again.

APCs remain in a resting state in the absence of danger signals that indicate the presence of a pathogen and/or tissue damage. In the resting state, the APCs express low levels of costimulatory molecules and cytokines that would otherwise cause T cell activation. This mechanism is known as peripheral tolerance and avoids the production of harmful immune responses against self-antigens. Only when "danger" is associated with antigen presentation would APCs mature to an "activating state", leading to T cell priming. Recent studies suggest that although tumor antigens are presented by antigen presenting cells, the antigens are not effective in inducing maturation of the antigen presenting cells. As a result, the antigen presenting cells do not express sufficient costimulatory molecules, and the T cells engaged by such antigen presenting cells become tolerant to the antigen being presented.

Vaccination against cancer has been explored to eradicate tumor cells. In order for tumor cells to survive and proliferate, they must be able to avoid and/or overcome the immune system of the host. For example, induction of antigen specific $CD4^+$ T cell tolerance is one of the mechanisms by which tumor cells overcome immune responses. Therefore, it is desirable to develop a vaccine that is capable of inhibiting tolerance or activating T cells that have escaped tolerance induction due to their low affinity for the tumor antigens.

SUMMARY

The present invention provides adjuvants, vaccines and related methods that are useful in eliciting immune responses, particularly immune responses against tumor antigens. We discovered that flagellin is capable of inhibiting tolerance when it is administered in conjunction with a tolerogenic antigen. This effect is likely mediated by the ability of flagellin to induce IL-12 while keeping IL-10 levels low. Furthermore, flagellin can be provided in an extended-releasing manner by using a flagellin-expressing cell. Preferably, the flagellin-expressing cell is treated such that it is no longer capable of replicating, yet retains the ability to express flagellin for a period of time, such as by lethal irradiation.

Accordingly, one aspect of the present invention provides a composition comprising a flagellin-expressing cell, wherein the cell has been lethally irradiated. This composition is useful as an adjuvant, and as an inhibitor of immune tolerance.

The flagellin-expressing cell may be any eukaryotic cell, preferably a vertebrate cell, such as a mammalian or avian cell. The flagellin-expressing cell may lack MHC class I molecules, MHC class II molecules, or both. In some embodiments, the flagellin-expressing cell is a B78-H1 cell or K562 cell that has been transfected with a flagellin gene.

The flagellin may be any flagellin. For example, the flagellin may be the flagellin of *Escherichia, Salmonella, Proteus, Pseudomonas, Bacillus, Campylobacter, Vibrio, Treponema, Legionella, Clostridia*, or *Caulobacter* spp.

The composition may optionally comprise an antigen that is associated with a tumor cell. The tumor cell may be from a tumor selected from the group consisting of leukemia, lymphoma, lung cancer, prostate cancer, colorectal cancer, thyroid cancer, renal cancer, adrenal cancer, liver cancer, pancreatic cancer, breast cancer and central and peripheral nervous system cancer. The use of antigens from other tumor cells, either benign or malignant, is also contemplated. The antigen may be any portion of the tumor cell, or the tumor cell itself. The tumor cell may be lethally irradiated.

The flagellin-expressing cell and the tumor cell may be from the same species, such as human, or from different species. The flagellin-expressing cell and the tumor cell may be derived from the same individual. In some embodiments, the flagellin-expressing cell may be the tumor cell that has been harvested from the subject and transfected with a flagellin gene.

Another aspect of the present invention provides a method for preparing an adjuvant, comprising lethally irradiating a flagellin-expressing cell.

A further aspect of the invention provides a method for preparing a vaccine against a tumor, comprising lethally irradiating a flagellin-expressing cell, and combining an antigen that is associated with the tumor. The antigen may be a tumor cell from the tumor, and the tumor cell may be optionally lethally irradiated.

Also provided is a method for treating a tumor in a subject, comprising administering to the subject an antigen that is associated with the tumor and an adjuvant to elicit an immune response against the tumor, wherein the adjuvant comprises a flagellin-expressing cell. The adjuvant may be administered at the same time or different time as the antigen. The adjuvant and/or the antigen may be administered only once or multiple times. The flagellin-expressing cell is preferably lethally irradiated before being administered. The adjuvant and the antigen may be administered in a composition prepared by combining the adjuvant and the antigen, and lethally irradiating the composition.

Another aspect of the invention provides a method for inducing the production of IL-12 in a subject, comprising administering to the subject a flagellin-expressing cell.

Yet another aspect of the invention provides a method of inhibiting tolerance to a tumor in a subject, comprising administering to the subject an antigen that is associated with the tumor and a flagellin-expressing cell.

Still another aspect of the invention provides a method for screening for a candidate compound that inhibits immune tolerance, said method comprising:
(a) providing an antigen-presenting cell;
(b) contacting the antigen-presenting cell with a test compound;
(c) detecting IL-10 and IL-12 produced by the antigen-producing cell, wherein induction of IL-12 without a cognate induction of IL-10 by the test compound indicates that the test compound is a candidate compound. Once candidate compounds are identified, they can be subject to further tests to determine their efficacy in inhibiting immune tolerance.

In any method provided by the present invention, as with any composition of the invention, the flagellin-expressing cell may be any eukaryotic cell, preferably a vertebrate cell, such as a mammalian or avian cell. The flagellin-expressing cell may lack MHC class I molecules, MHC class II molecules, or both. In some embodiments, the flagellin-expressing cell is a B78-H1 cell or K562 cell that has been transfected with a flagellin gene. The flagellin may be any flagellin. For example, the flagellin may be the flagellin of *Escherichia, Salmonella, Proteus, Pseudomonas, Bacillus, Campylobacter, Vibrio, Treponema, Legionella, Clostridia,* or *Caulobacter* spp.

The antigen may be any portion of a tumor cell, or the tumor cell itself. The tumor cell may be lethally irradiated. Any tumor cell of interest may be employed. For example, the tumor cell may be from a tumor selected from the group consisting of leukemia, lymphoma, lung cancer, prostate cancer, colorectal cancer, thyroid cancer, renal cancer, adrenal cancer, liver cancer, pancreatic cancer, breast cancer and central and peripheral nervous system cancer.

The flagellin-expressing cell and the tumor cell may be from the same species, such as human, or different species. The flagellin-expressing cell and the tumor cell may be derived from the same individual. In some embodiments, the flagellin-expressing cell may be the tumor cell that has been transfected with a flagellin gene.

The details of one or more embodiments of the invention are set forth in the accompanying drawings and the description below. Other features, objects, and advantages of the invention will be apparent from the description and drawings, and from the claims.

3A and 3B: Peritoneal macrophages were treated for 24 hours with the indicated concentrations of flagellin (3B) or lipopolysaccharide (LPS) (3A) and the supernatants analyzed by ELISA to detect the presence of IL-12p40/70 and IL-10.

3C: Peritoneal macrophages were treated with 5 μg/ml of flagellin and the supernatants harvested for ELISA analysis at the indicated times. LPS (1 μg/ml) served as a positive control, and Hank's Balanced Salt Solution (HBSS) was the vehicle used to deliver LPS and flagellin.

Figure 4:
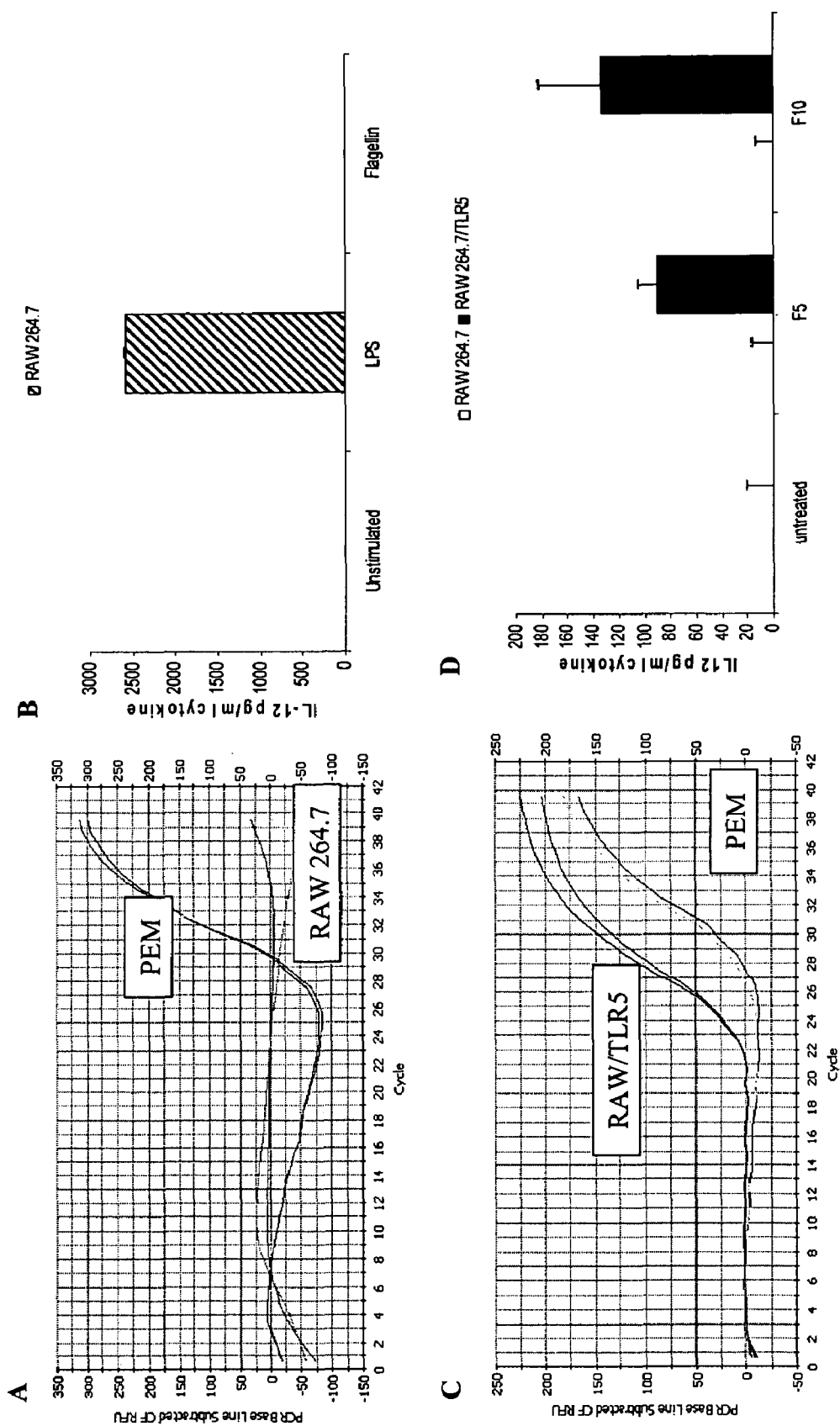

FIG. 4. Flagellin induced IL-12 production is dependent on the presence of toll-like receptor 5 (TLR5).

4A: TLR5 mRNA transcripts were not detected using real time RT PCR in the murine macrophage cell line RAW 264.7.

4B: RAW 264.7 cells did not produce IL-12 when treated with flagellin.

4C: TLR5 mRNA expression was detected in RAW 264.7 cells stably transfected with a construct encoding murine TLR5.

4D: RAW 264.7 cells stably transfected with TLR5 produced IL-12 in response to flagellin as detected by ELISA. F5, cells stimulated by 5 μg/ml of flagellin. F10, cells stimulated by 10 μg/ml of flagellin.

The data from real time RT-PCR are obtained from samples with identical quantities of GAPDH mRNA, the house keeping gene that served as loading control.

Figure 5:
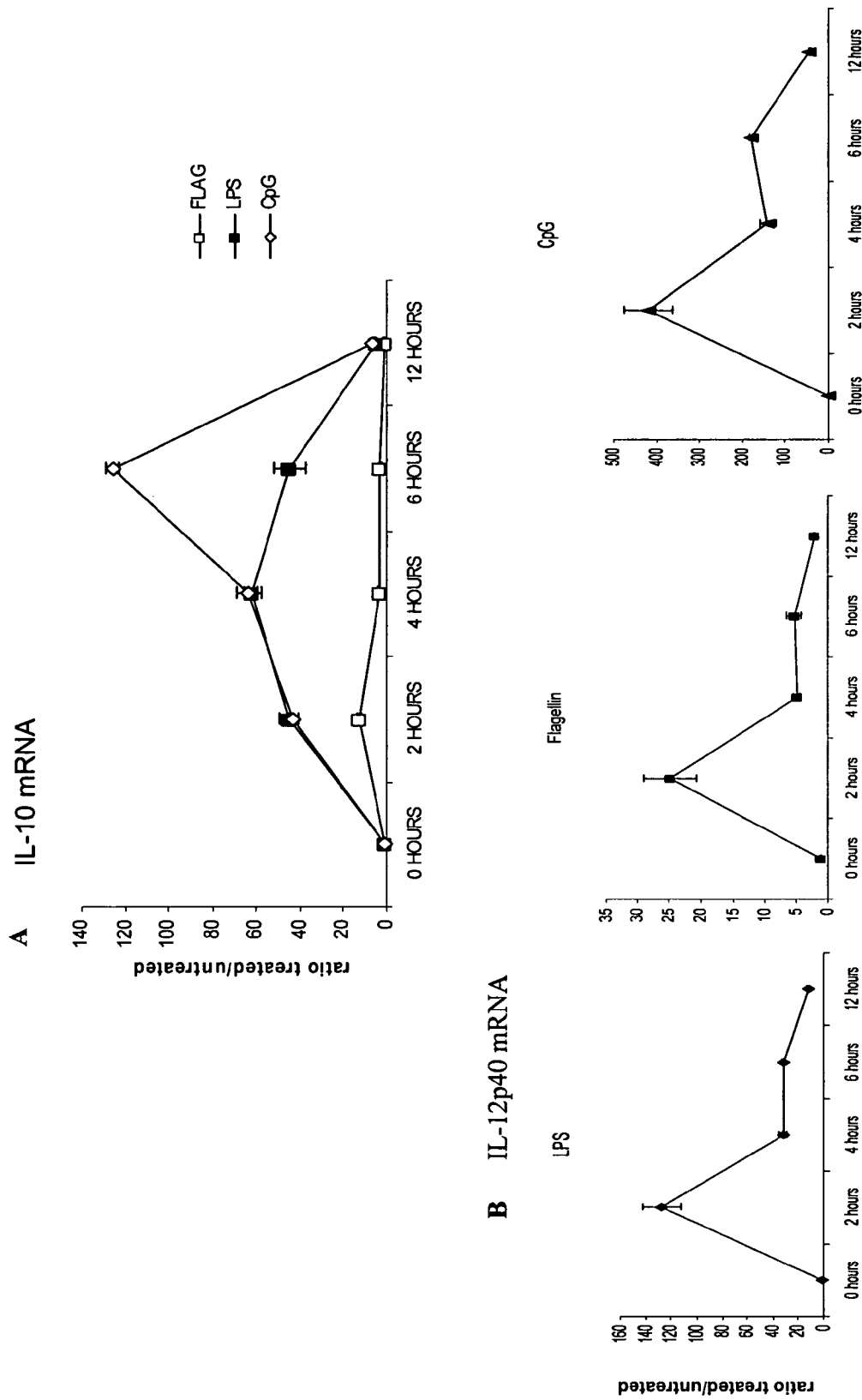

FIG. 5. IL-10 mRNA was weakly and transiently induced upon stimulation of PEM with flagellin.

5A shows the dynamics of the mRNA as indicated upon stimulation with the three different TLR ligands. The mRNA levels in treated cells were normalized to those of untreated cells. FLAG, flagellin.

5B shows the temporal pattern IL-12p40 mRNA upon treatment with the different TLR ligands.

Figure 6:
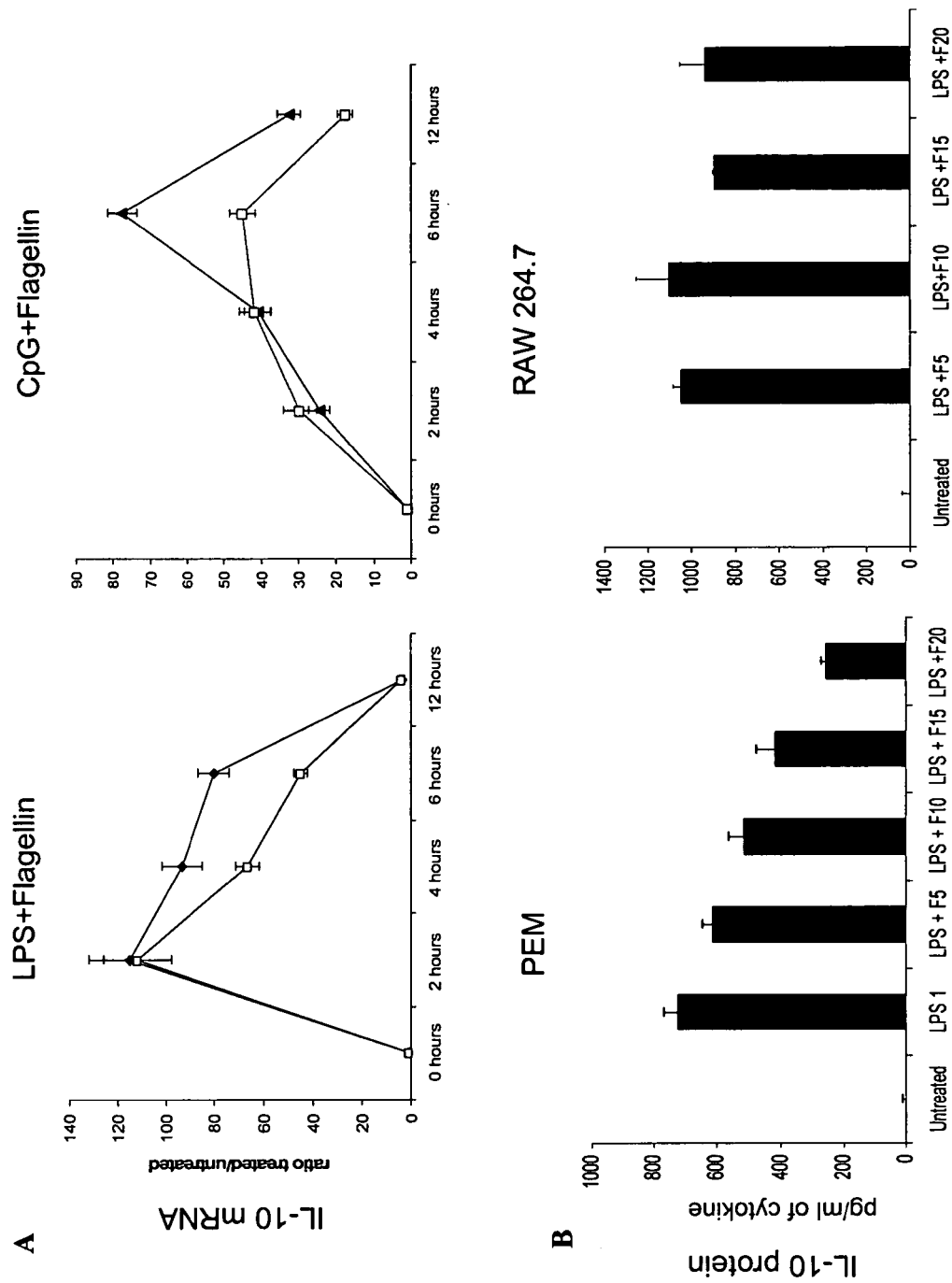

FIG. 6. Flagellin inhibits the production of IL-10 mRNA and protein elicited by LPS or CpG.

6A: PEM were treated with LPS (1 μg/ml) or CpG (2 μM) in the presence or absence of flagellin (20 μg/ml) for the indicated periods of time, and IL-10 mRNA level was determined. Open squares, with flagellin. Closed diamonds or triangles, without flagellin.

6B: PEM or RAW 264.7 cells were treated with increasing concentrations of flagellin (5, 10, 15 or 20 μg/ml; "F5", "F10", "F15" or "F20") plus a constant concentration of LPS (1 μg/ml; "LPS 1" or "LPS") for 24 hours, then the supernatants were analyzed by ELISA for IL-10 protein.

Figure 7:
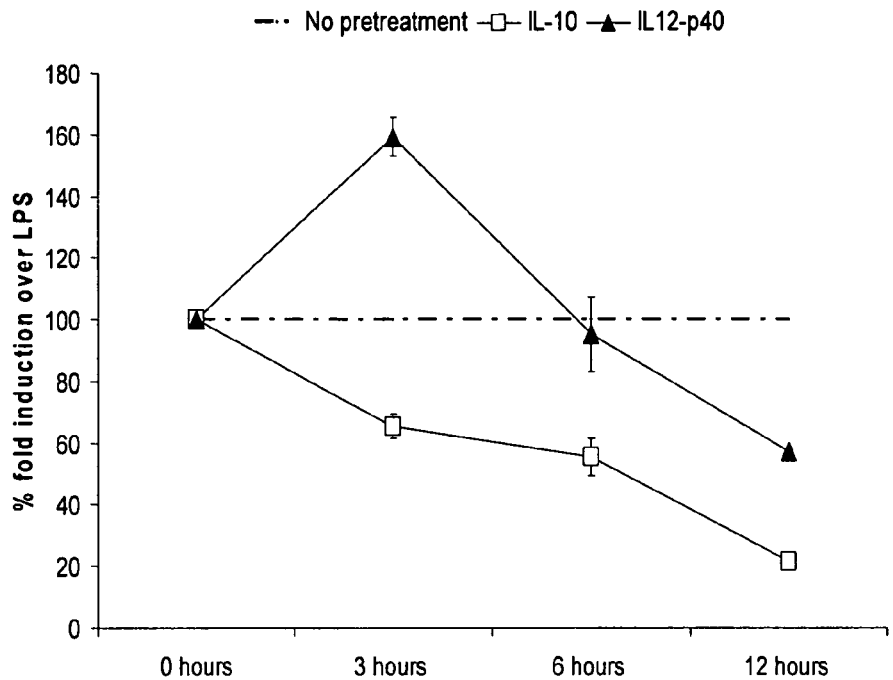
Figure 7:
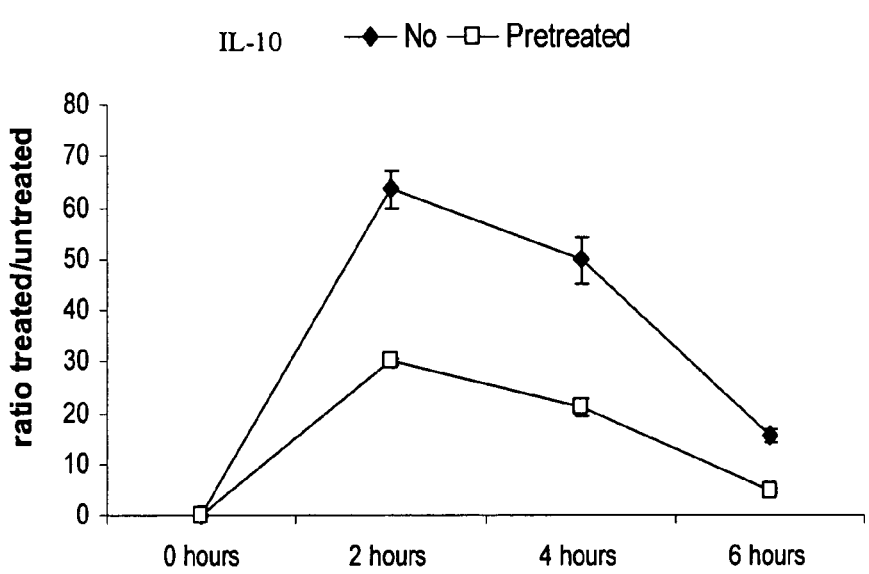
Figure 7:
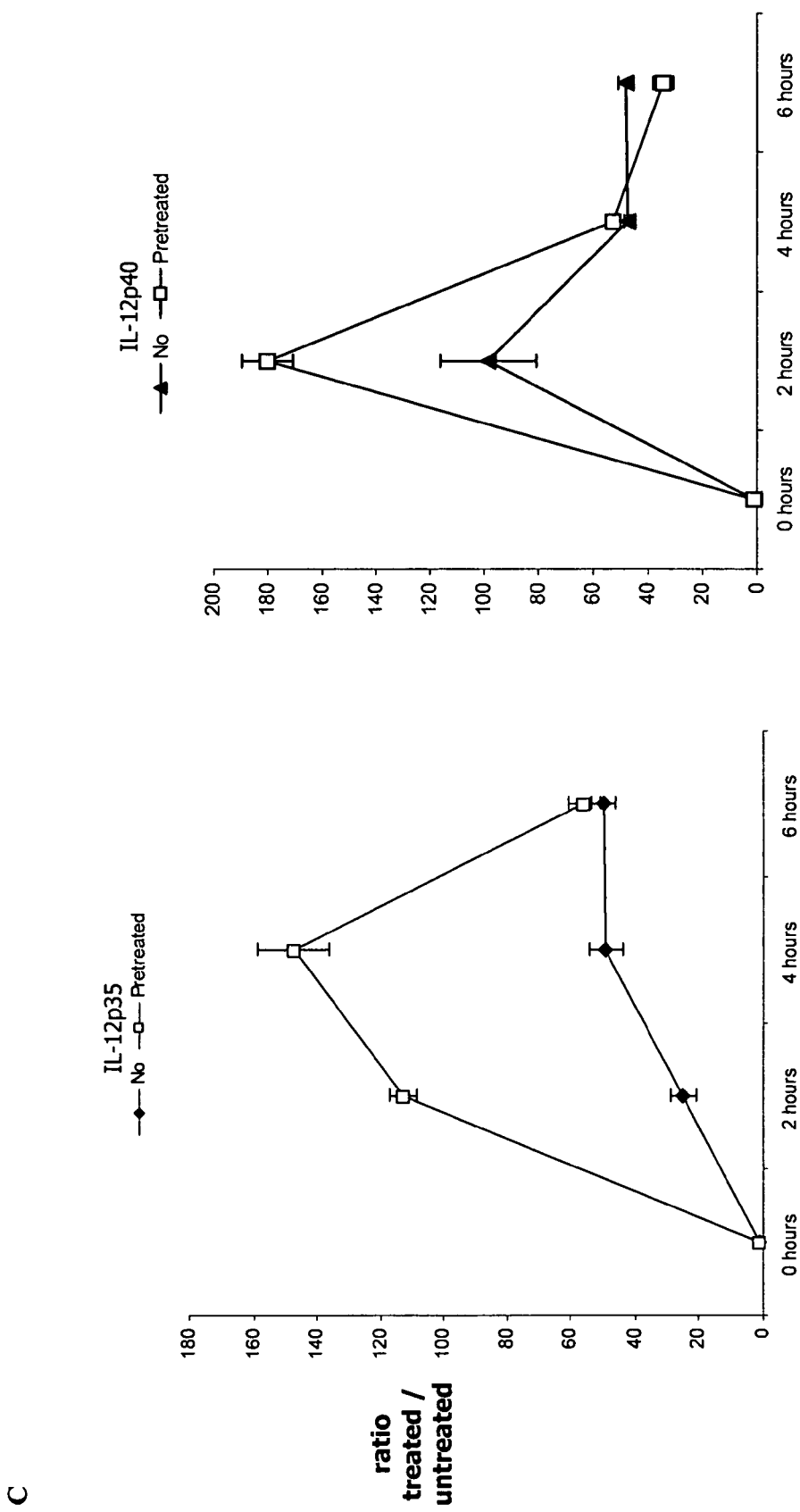

FIG. 7. The effect of incubation time on cytokine production upon stimulation of macrophages by flagellin in combination with other TLR ligands.

7A: PEM were stimulated with 5 μg/ml flagellin for 0, 3, 6 or 12 hours, and afterwards LPS was added to the media (final concentration 1 μg/ml). After 2 hours of LPS stimulation, the cells were harvested and IL-10 and IL-12 RNA analyzed.

7B and 7C show the dynamics of LPS induced IL-12p40 and IL-12p35 mRNAs in cells pretreated with flagellin for 3 hours (open symbols), compared with cells that were not pre-treated with flagellin (closed symbols).

Figure 8:
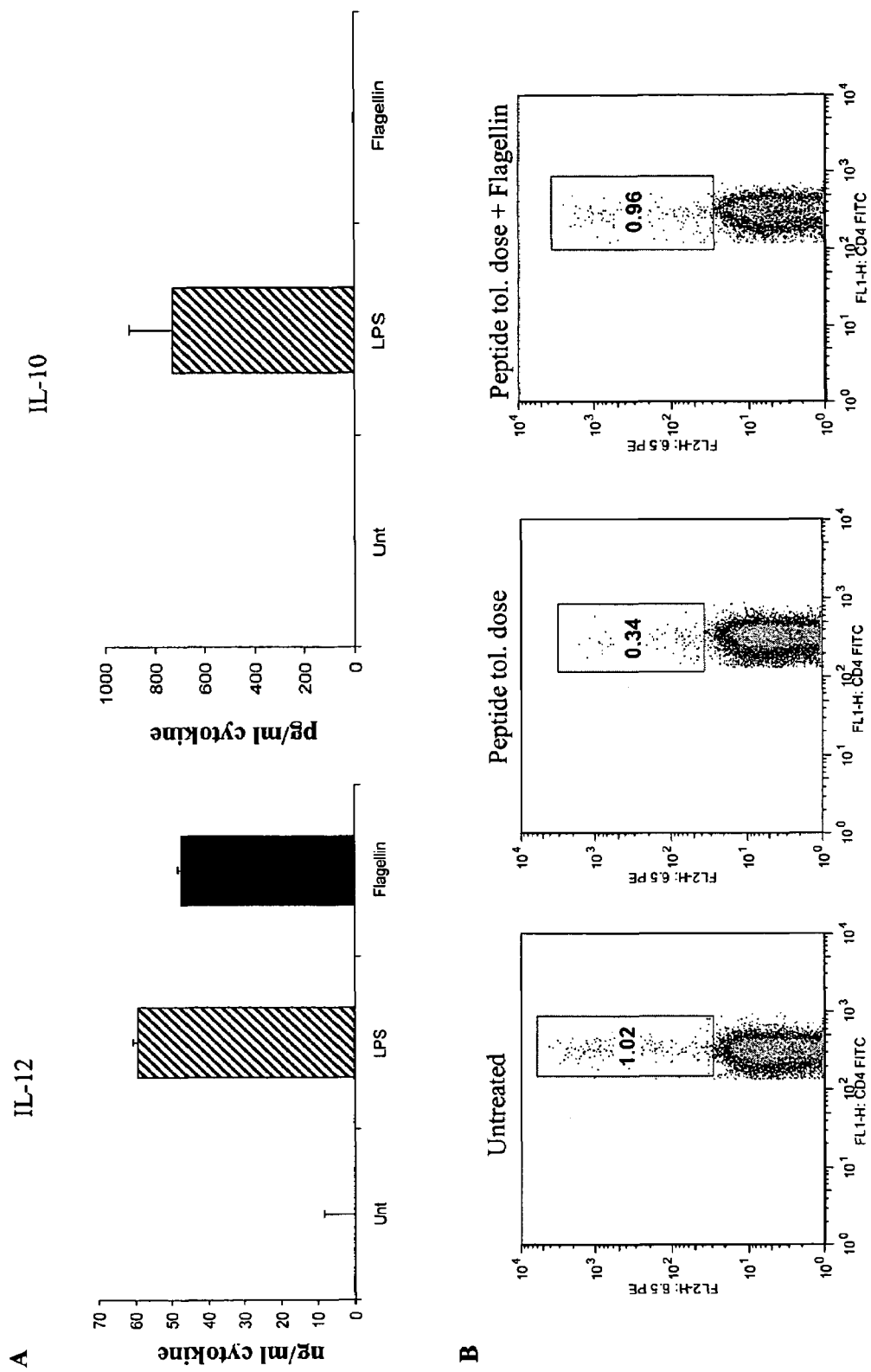
Figure 8:
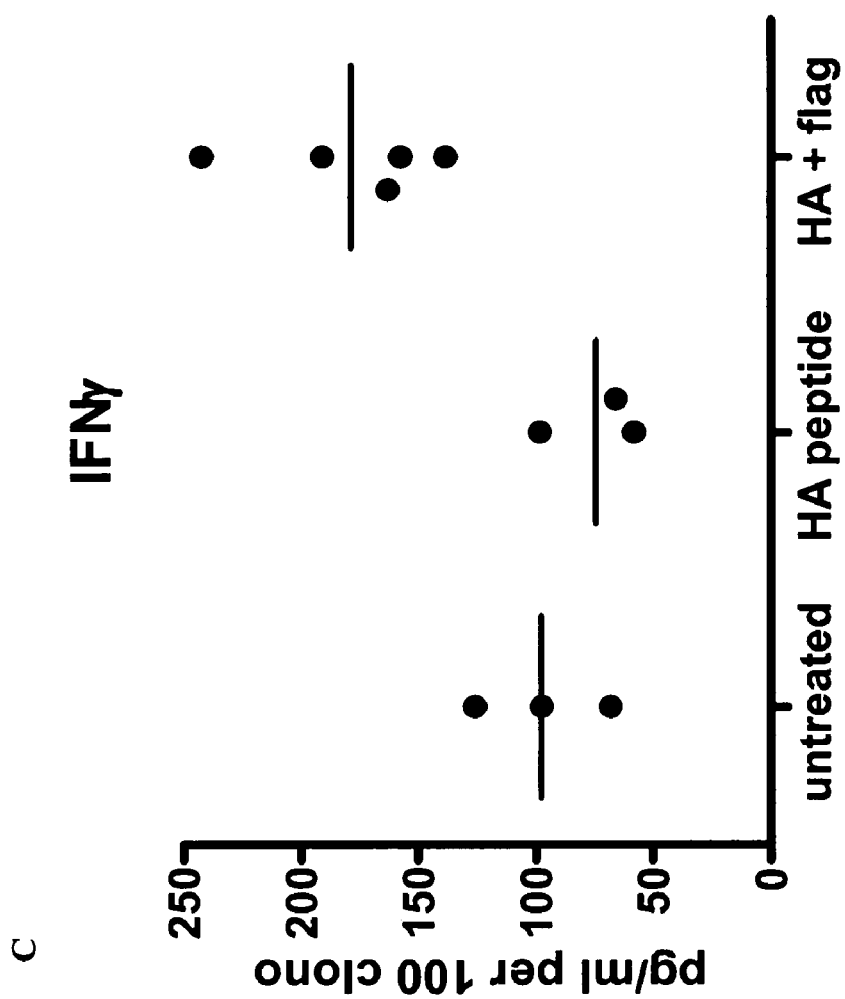

FIG. 8. In vivo effects of flagellin treatment.

8A shows the serum levels of IL-12p40/p70 and IL-10 in BALB/c mice treated with 30 μg of flagellin or LPS. Unt, untreated.

8B shows the percentage of clonotypic 6.5 T cells in the spleens of control animals or animals that were I.V. injected with a tolerogenic dose of HA peptide (200 µg) with or without 10 µg of flagellin.

8C shows IFNγ production per 100 clonotypic T cells after whole splenocytes had been incubated in vitro for 48 hours with the HA peptide. Each dot represents an animal and the bar shows the group average.

Figure 9:
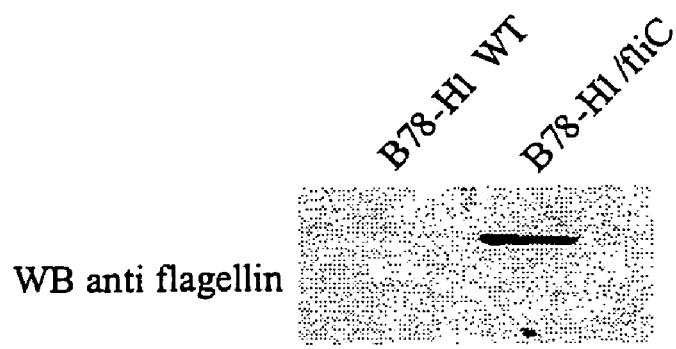
Figure 9:
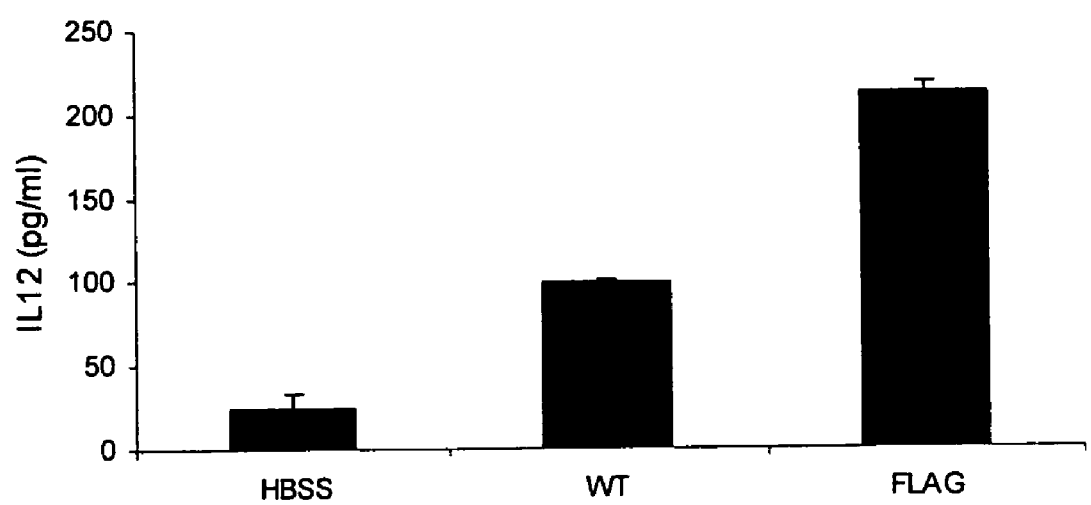

FIG. 9. Flagellin-expressing cells are also able to stimulate the production of IL-12 by PEM.

9A shows the production of flagellin by B78-H1 cells transfected with a construct expressing the fliC gene from *S. typhimurium*.

9B shows the production of IL-12p40/p70 cytokine by PEM upon 24 hours of treatment with the lysates from B78-H1 cells transfected (FLAG) or untransfected (WT) with the fliC expressing construct. HBSS shows the results from vehicle-treated PEMs.

DETAILED DESCRIPTION

The present invention provides adjuvants, vaccines and related methods that are useful in eliciting immune responses, particularly immune responses against tumor antigens. We discovered that flagellin is capable of inhibiting tolerance when it is administered in conjunction with a tolerogenic antigen. This effect is likely mediated by the ability of flagellin to induce IL-12 while keeping IL-10 levels low. Furthermore, flagellin can be provided in an extended-releasing manner by using a flagellin-expressing cell. Preferably, the flagellin-expressing cell is treated such that it is no longer capable of replicating, yet retaining the ability to express flagellin, such as by lethal irradiation.

Prior to describing the invention in further detail, the terms used in this application are defined as follows unless otherwise indicated.

Definitions

An "adjuvant" is a substance that is capable of enhancing an immune response to an antigen. The immune response may be enhanced by accelerating, prolonging, or increasing the magnitude of the immune response.

An "antigen" is a substance that can be recognized by an antibody, B cell or T cell. An antigen can be a crude mixture of molecules, such as a cell, or one or more isolated molecules. Examples of crude antigens include attenuated organisms, inactivated organisms, viral particles and tumor cells. Examples of isolated antigens include a polypeptide, lipoprotein, glycoprotein, lipid, toxoid, polysaccharide, capsular polysaccharide and nucleic acid. Such isolated antigens can be naturally occurring, recombinantly produced, or synthesized. Exemplary naturally occurring antigens include purified microbial and tumor cell macromolecules. Exemplary recombinantly produced antigens include cloned microbial and tumor cell antigens. Exemplary synthesized antigens include synthetic peptides and nucleic acids.

An "antigen that is associated with a tumor cell" may be the tumor cell itself or any part of the tumor cell. For example, the antigen may be any extract of the tumor cell; any fraction of the tumor cell; one or more surface proteins, nuclear proteins, glycoproteins, lipids, or nucleic acids of the tumor cell; cytoplasmic membrane of the tumor cell; or any combination of the above. Similarly, an "antigen that is associated with a tumor" may comprise as at least one tumor cell, or part of any tumor cell, of the tumor.

An "effective amount" of a substance is an amount of the substance that is sufficient to achieve the intended effect. For example, an effective amount of a flagellin-expressing cell as an adjuvant is an amount of the cell that is sufficient, when administered in conjunction with an antigen, to enhance an immune response against the antigen. An effective amount of a vaccine for treating a tumor is an amount of the vaccine sufficient to alleviate or eliminate the symptoms of the tumor, or slowing down the progress of the tumor. The effective amount will vary with factors such as the nature of the substance, the route of administration, the formulation comprising the substance, and the size, species, and health condition of the recipient of the substance. Methods to determine the effective amount are known in the art.

A "flagellin" may be may be any polypeptide that binds a naturally occurring TLR5 and triggers at least one of the biological functions of the TLR5 in antigen-presenting cells upon such binding. Thus, a flagellin may be a polypeptide comprising any of the naturally occurring bacterial flagellin proteins. A flagellin may also be a polypeptide that is substantially identical with any of the naturally occurring bacterial flagellin proteins at the amino acid sequence level, wherein the polypeptide is capable of binding a naturally occurring TLR5. Furthermore, a flagellin may be a polypeptide that is substantially identical with the 170 residues from the N terminus and 90 residues from the C terminus of any of the naturally occurring bacterial flagellin proteins at the amino acid sequence level, wherein the polypeptide is capable of binding a naturally occurring TLR5. Any flagellin useful in this invention may be a fusion protein that comprises an unrelated peptide or protein, such as an antigen or the Fc portion of an immunoglobulin. The flagellin of this invention may also comprise a modification, such as glycosylation or phosphorylation.

Flagella are found primarily, although not exclusively, on the surface of rod and spiral shaped bacteria, including members of the genera *Escherichia, Salmonella, Proteus, Pseudomonas, Bacillus, Campylobacter, Vibrio, Treponema, Legionella, Clostridia*, and *Caulobacter*. Flagellin sequences from numerous bacteria are available in the art, such as Genbank accession numbers D13689, YP_275549, YP_275550, AAU18718, AAU18717, ZP_00743095, EAO52626, YP_315348, AAT28337, AAT28336, AAT28335, AAT28334, AAT28333, AAZ36356, AAZ33167, AAZ94424, AAZ91670, NP_414908, BAD18052, and BAD18051.

The flagellin proteins from different species exhibit a high degree of protein sequence homology at the amino and carboxy termini (about 170 residues from the N terminus and about 90 residues from the C terminus), and the presence of a polymorphic central region which is responsible for the antigenic diversity among different flagella. The conserved regions are important for TLR5 binding, while the polymorphic central region can be deleted without affecting binding to TLR5. Structural-function analyses of the flagellin proteins have been reported (see, e.g., Smith K D et al., Toll-like receptor 5 recognizes a conserved site on flagellin required for protofilament formation and bacterial motility, Nat Immunol. 2003 December; 4(12):1247-53; Murthy K G et al., Identification of conserved domains in *Salmonella* muenchen flagellin that are essential for its ability to activate TLR5 and to induce an inflammatory response in vitro, J Biol Chem. 2004 Feb. 13; 279(7):5667-75; U.S. Pat. No. 6,130,082; and U.S. Patent Application Publication No. 2003/0044429).

TLR5 sequences are also known in the art. For example, the human sequence has been disclosed as Genbank Accession No. NP_003259, BAB43955, or AAC34136 (partial). The mouse sequence has been disclosed as Genbank Accession No. AAF65625. The sequences for other species have also been published (such as Genbank Accession Nos. NP_001019757, BAD91800, AAZ04297, AAY58240, AAU95563, AAY21236, AAX56973, and AAO62341). TLR5 binding and biological activities can be assayed, for example, as disclosed in U.S. Patent Application Publication No. 2003/0044429 and Mizel S B et al., Identification of a sequence in human toll-like receptor 5 required for the binding of Gram-negative flagellin, Biol Chem. 2003 Jun. 27; 278(26):23624-23629.

A "flagellin-expressing cell" may be any eukaryotic cell that expresses a flagellin. The cell may be a vertebrate cell, such as a mammalian or avian cell, preferably a human, rat, mouse, rabbit, rodent, dog, cat, horse, cattle, sheep, goat, pig, chicken, or non-human primate cell.

An "immune response" is the change of the immune system in response to an antigen, usually with the ultimate result of eliminating, neutralizing, or degradation of the antigen. An immune response may be humoral or cellular.

A substance can "inhibit tolerance to an antigen" if the antigen, in the absence of the substance, does not elicit an immune response or elicits only a low level of immune response, while in the presence of the substance the antigen can elicit a significantly stronger immune response. Preferably, the substance can increase the immune response to the antigen by at least 40%, 50%, 60%, 70%, 80%, 90%, 100%, 150%, 200%, 250%, or 300%. The immune response may be a humoral or cellular response, and can be detected or measured by any methods established in the art. These methods may include, without being limited to, measuring antibody levels (e.g., ELISA, RIA), determining the number of B or T cells specific for the antigen, and measuring the level of cytokines.

A cell is "lethally irradiated" if the cell, after the irradiation, is not capable of replicating (i.e., dividing into two or more cells). Art-recognized methods can be used to determine the dose of radiation and whether the irradiated cells can replicate. For example, cells growing at a density of $5\times10^5$ cells/ml can be irradiated with 10,000 Rads, then viable cell numbers can be determined over time by, e.g., Trypan blue exclusion. To be useful in the present invention, the lethally irradiated cell should preferably be able to continue to express proteins for a period of time (see, e.g., Borrello I et al., A universal granulocyte-macrophage colony-stimulating factor-producing bystander cell line for use in the formulation of autologous tumor cell-based vaccines, Hum Gene Ther. 1999 Aug. 10; 10(12):1983-1991). Protein expression by the lethally irradiated cells can be assayed by methods known in the art, such as gel electrophoresis and protein staining for protein synthesis in general, or Western analysis for specific protein(s).

As used herein, the term "malignancy" refers to a non-benign tumor or a cancer. A cancer is a type of hyperproliferative disease which includes a malignancy characterized by deregulated or uncontrolled cell growth. Malignant tumors can be broadly classified into three major types. Malignant tumors arising from epithelial structures are called carcinomas, malignant tumors that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to neurofibromatosis. Examples of cancer include, but are not limited to, carcinoma, lymphoma, blastoma, sarcoma, and leukemia or lymphoid malignancies. More particular examples of cancers include: squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer (including gastrointestinal cancer, pancreatic cancer), glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. A cancer includes primary malignant cells (e.g., those that have not migrated to sites in the subject's body other than the site of the original malignancy) and secondary malignant cells (e.g., those arising from metastasis, the migration of malignant cells to secondary sites that are different from the site of the original tumor).

The term "substantially identical", at the amino acid sequence level, means that the sequence identity of two amino acid sequences is at least 30%, 40%, 50%, 60%, 70%, 80%, 85%, 90%, 95%, 98% or 99%.

"Sequence identity" is the percentage of residues in an amino acid or nucleic acid sequence that are identical after aligning the sequence with a reference sequence and introducing gaps, if necessary, to achieve maximal sequence identity. Methods and computer programs for the alignment, such as BLAST, are well known in the art. For example, if a polypeptide is substantially identical with the 170 residues from the N terminus and 90 residues from the C terminus of a naturally occurring bacterial flagellin, then when the polypeptide and the reference sequence (170 residues from the N terminus and 90 residues from the C terminus of the naturally occurring bacterial flagellin) are maximally aligned, at least 30% of the amino acids in the reference sequence are found in the corresponding positions in the polypeptide.

A "tolerogenic antigen" is an antigen that, by itself, elicits tolerance rather than an immune response by the immune system.

A cell is "transfected" with a protein if a nucleic acid encoding the protein is introduced into the cell. Similarly, a cell is "transfected" with a nucleic acid if the nucleic acid is introduced into the cell. Methods of introducing nucleic acids into cells are known in the art, such as lipofection, electroporation, calcium phosphate precipitation, and microinjection. The transfection may be transient or stable.

"Treating" a tumor means alleviating or eliminating the symptoms of a tumor, or slowing down the progress of the tumor. The alleviating or eliminating effect can be determined by any method known in the art, such as measuring the size of the tumor and observing biochemical indicators of the particular tumor. For example, a subject is treated if showing one or more of the following: reduction in the number of cancer cells; reduction in the tumor size; inhibition or elimination of cancer cell infiltration into peripheral organs, including the spread of cancer into soft tissue and bone; inhibition or elimination of tumor metastasis; inhibition of tumor growth; reduction of one or more of the symptoms associated with the specific cancer; and reduced morbidity and mortality. The alleviation is preferably at least about 10%, more preferably at least about 20%, 30%, 40%, 50%, 60%, 70%, 80% or 90%.

A "tumor cell", also known as a "neoplastic cell", refers to a cell which proliferates at an abnormally high rate. A new growth comprising tumor cells is a tumor, also known as a neoplasm. A tumor is an abnormal tissue growth, generally forming a distinct mass, that grows by cellular proliferation more rapidly than normal tissue growth. A tumor may show partial or total lack of structural organization and functional coordination with normal tissue. As used herein, a tumor is intended to encompass hematopoietic tumors as well as solid tumors. A tumor may be benign (benign tumor) or malignant (malignant tumor or cancer). A tumor or tumor tissue may also comprise non-tumor cells, e.g., vascular cells which form blood vessels to supply the tumor or tumor tissue.

A "vaccine" is a composition that comprises at least one antigen and, when administered to an animal bearing an immune system, can elicit an immune response against the antigen. A vaccine can contain isolated or crude antigen, and can contain one or more antigens. A vaccine can also contain one or more adjuvants.

Methods and Compositions

Pathogens express molecules known as pathogen associated molecular patterns (PAMPs), which serve as danger signals to APCs. Some of these signals are unique products of microbial metabolism, such as LPS or lipoproteins, or highly conserved features of particular microorganisms, such as CpG DNA motifs or bacterial flagellin. These molecules are ligands of the toll-like receptors (TLRs) of APCs. Toll-like receptors are evolutionary conserved, germline encoded receptors, expressed primarily on macrophages and dendritic cells that recognize PAMPs. Recognition of PAMPs by TLRs leads to the activation of NFkB transcription factors and members of the mitogen-activated protein kinase (MAP kinase) family, and ultimately results in the activation of these APCs.

Flagellin, the ligand of TLR5, is the basic element of bacterial flagella. Bacterial motility depends on the flagellum, an extracellular propeller consisting of several thousands of flagellin units. The presence of flagella is strongly related with the infectivity of some pathogenic bacteria. In addition to giving these bacteria the ability to move in the aqueous environment, the flagellum also aids to the attachment to host cells, thereby contributing to the virulence of pathogenic microorganisms. Consistent with its role as TLR5 ligand, flagellin has recently been shown to work as a potent adjuvant of T cell function in vitro and in vivo (McSorley S J et al., Bacterial flagellin is an effective adjuvant for CD4+ T cells in vivo, J Immunol 2002 Oct. 1; 169(7):3914-9).

We hypothesized that flagellin can provide a "danger" signal to activate APCs in tumor antigen presentation, thereby inhibiting T cell tolerance to the tumor antigen. To this end, we first tested the adjuvant function of our flagelllin preparation, and confirmed that it was capable of increasing the production of IFNγ and IL-2 (Example 1). Next we determined whether in vivo treatment using flagellin would prevent antigen specific T cell tolerance induced by high doses of antigens. As shown by Example 2, T cell responses were almost completely abrogated in the animals treated with a tolerogenic dose of the antigen. In contrast, the mice injected with the same dose of antigen and flagellin yielded significant levels of T cell response. These results indicate that flagellin has preserved the capacity of T cells to respond to tolerogenic levels of antigens. Consistent with a role of flagellin to activate APCs and inhibit tolerance, peritoneal macrophages treated with flagellin displayed higher levels of B7.1, CD40 and MHC class I molecules as compared with untreated macrophages (Example 3).

Anti-inflammatory cytokines like IL-10-influence the T cell decision toward an anergy response. Inflammatory cytokines such as IL-12 play the opposite role, inducing T cell differentiation into a helper T cell that will drive an adaptive immune response against the antigen presented by the APC. We further discovered that flagellin can induce the production of IL-12 while keeping IL-10 levels low (Example 4). Thus, it is contemplated that flagellin changes the balance between anti-inflammatory cytokines and inflammatory cytokines to inhibit tolerance.

Flagellin-induced IL-12 production depends on the presence of the receptor for flagellin, TLR5 (Example 5). In contrast to flagellin, LPS (TLR4 ligand) and CpG (TLR9 ligand), stimulated both IL-12 and IL-10 (Examples 4 and 6). Furthermore, flagellin is capable of inhibiting the effect of LPS and CpG in inducing IL-10 (Example 7). Therefore, although PAMPs are known as danger signals to APCs, not all of them can tip the balance between anti-inflammatory cytokines and inflammatory cytokines to inhibit tolerance. Flagellin not only leads to tolerance prevention, but also directs the actions of other PAMPs in this regard. The effect of flagellin was further confirmed by in vivo experiments (Example 8). Accordingly, the present invention provides a method for inhibiting tolerance in a subject to an antigen by providing a flagellin and the antigen to the subject.

We explored a new formulation to deliver flagellin by using a flagellin-expressing cell, which can provide flagellin to the subject in a continuous mode. Therefore, we constructed a flagellin-expressing cell and showed that the lysates of this cell can enhance IL-12 production (Example 9). It is contemplated that the flagellin-expressing cell can optionally be treated before administration in a manner that would prevent the cell from replicating, while retaining the ability of the cell to express flagellin. A lethal irradiation is an example of such a treatment. Thus, the flagellin is preferably provided by administering a flagellin-expressing cell to the subject. In particular, the flagellin-expressing cell can be first lethally irradiated so that is would not replicate in the body of the subject, yet it can continue to express flagellin, e.g., for a few days.

The flagellin-expressing cell may be any eukaryotic cell, preferably a vertebrate cell, such as a mammalian or avian cell. The cell may be a normal cell, a tumor cell, a fetal cell, an adult cell, from an established cell line, or from a primary culture. The cell is preferably from the same species as the subject receiving the cell. In some embodiments, the cell may be from the subject. Exemplary sources of the cell include, but are not limited to, human, rat, mouse, rabbit, rodent, dog, cat, horse, cattle, sheep, goat, pig, chicken, or non-human primate.

An advantage of using a flagellin-expressing cell from the same species as the subject is to avoid massive immune responses against the cross-species cell (xeno-responses). Even if a flagellin-expressing cell from the same species is used, immune responses against a different individual of the same species (allo-responses) may still divert the immune system and quickly eliminate the flagellin-expressing cell. One way of avoiding this problem is to use a flagellin-expressing cell that lacks MHC class I molecules, MHC class II molecules, or both. For example, B78-H1 cells and K562 cells are murine and human cells, respectively, that lack the MHC class I and class II molecules.

Flagellin sequences are readily obtainable based on knowledge in the art. In fact, the flagellin sequences from numerous bacterial species, as well as structural analyses, have been published. Any polypeptide with flagellin function, namely one that binds a naturally occurring TLR5 and triggers at least one of the biological functions of the TLR5 in antigen-presenting cells upon such binding, can be used in the present invention. These include polypeptides comprising any of the naturally occurring bacterial flagellin proteins, and polypeptides that are substantially identical with any of the naturally occurring bacterial flagellin proteins at the amino acid sequence level, wherein the polypeptides are capable of binding a naturally occurring TLR5.

Methods of transfecting cells are also well known in the art. These methods include, but are not limited to, transfection, microinjection, scrape-loading, and receptor-mediated uptake by the cell. Transfection may be transient or stable. Exemplary current methods of transfection include calcium phosphate precipitation, electroporation, lipofection, and peptide-mediated transfection. Ballistic DNA delivery and transduction (i.e., the introduction of foreign DNA by virus or virus vector infection) can also be employed.

For example, a flagellin can be delivered to cells by means of an expression vector. Suitable expression vectors comprise a promoter that is active in the cells in which the flagellin is to be expressed. Expression vectors useful for practicing the invention may also include selectable markers, cell-type or cell-cycle-specific enhancers or repressors, polylinkers, start codons, ribosome binding sites, internal ribosome entry sites, introns, stop codons, polyadenylation signals, or other features that facilitate cloning and vector stability, mRNA stability and localization in the cell, and translation efficiency, or combinations thereof. Expression vectors include viral expression vectors. Selection of these features is largely based on the cells to be transfected, and the expression characteristics desired. A large number of commercially available vectors are available for expressing polypeptides in cells.

For localization in the cell, it is contemplated that the flagellin may be engineered to contain the motif YXXØ (SEQ ID NO:1: Y is tyrosine, X is any amino acid, and Ø is an amino acid with a bulky hydrophobic side chain). This motif has been shown as responsible for targeting the lysosomal membrane protein LAMPI (Lysosomal associated membrane protein one) to the lysosomal compartment. It is also present in other proteins localized on the lysosome membrane, such as LAP (lysosomal acid phosphatase) and LAMP2, and is able to target by itself the CD44 protein, a cellular membrane receptor, to the lysosomal compartment.

The antigen of the present invention may be any antigen of interest. In particular, the antigen may be an antigen that is associated with a tumor. For example, the antigen may be a tumor cell to which an immune response is desired, or it may be part of the tumor cell, such as any extract of the tumor cell; any fraction of the tumor cell; one or more surface proteins, nuclear proteins, glycoproteins, lipids, or nucleic acids of the tumor cell; cytoplasmic membrane of the tumor cell; or any combination of the above. The antigen may be naturally occurring, recombinantly produced, or synthesized. A preferred antigen comprises tumor cells from the tumor to which an immune response is desired. For example, a biopsy sample from a tumor, harvested from a subject bearing the tumor, can be processed and used as an antigen in a vaccine for treating the tumor. Preferably, tumor cells are lethally irradiated before being administered as an antigen.

The flagellin-expressing cell and/or the antigen can be administered by a variety of routes to stimulate an immune response. For example, they can be delivered intranasally, subcutaneously, intradermally, intralymphatically, intramuscularly, intratumorally, orally, intravascularly, intraperitoneally and intracerebrally. Nasal delivery routes may be useful for inducing both mucosal and systemic immune responses. Those skilled in the art will know how to select appropriate delivery routes for particular formulations of flagellin-expressing cell and/or antigen.

Compositions of this invention can be administered to a subject as a pharmaceutical composition comprising a pharmaceutically acceptable carrier and the active ingredient (e.g., flagellin-expressing cell and/or antigen). The choice of pharmaceutically acceptable carrier depends on the route of administration of the pharmaceutical composition and the particular physical and chemical characteristics of the flagellin-expressing cell/antigen. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the active ingredient, increase its solubility, or increase its absorption. Such physiologically acceptable compounds include carbohydrates such as glucose, sucrose or dextrans; antioxidants, such as ascorbic acid or glutathione; chelating agents; and low molecular weight proteins. Other suitable formulations for use in the present invention can be found in Remington's Pharmaceutical Sciences (Gennaro, A. R. ed. (2000) Remington's Pharmaceutical Sciences, 20th edition. Williams & Wilkins Pa., U.S.A.).

Another aspect of the present invention provides a method for preparing an adjuvant, wherein the adjuvant comprises a flagellin-expressing cell. The flagellin-expressing cell is preferably lethally irradiated. The adjuvant can be used to enhance the immune response to an antigen, particularly an antigen that is associated with a tumor. The resulting adjuvants are also provided in the present invention.

A further aspect of the invention provides a method for preparing a vaccine against a tumor, comprising lethally irradiating a composition that comprises a flagellin-expressing cell, and combining the composition with an antigen that is associated with the tumor.

Also provided is a method for treating a tumor in a subject, comprising administering to the subject an antigen that is associated with the tumor and an adjuvant to elicit an immune response against the tumor, wherein the adjuvant comprises a flagellin-expressing cell. The adjuvant may be administered at the same time or different time as the antigen. Either the adjuvant or the antigen may be administered only once or multiple times. The flagellin-expressing cell is preferably lethally irradiated before being administered. The adjuvant and the antigen may be administered in a composition prepared by combining the adjuvant and the antigen, and lethally irradiating the composition.

Another aspect of the invention provides a method for inducing the production of IL-12 in a subject, comprising administering to the subject a flagellin-expressing cell. It is contemplated that the flagellin-expressing cell does not induce, or induces only a low level of, IL-10. Furthermore, the flagellin-expressing cell has the effect of reducing IL-10 production that is induced by other stimuli in the subject.

Yet another aspect of the invention provides a method for inhibiting tolerance to a tumor in a subject, comprising administering to the subject an antigen that is associated with the tumor and a flagellin-expressing cell.

Still another aspect of the invention provides a method of screening for a candidate compound that inhibits immune tolerance, said method comprising:
(a) providing an antigen-presenting cell;
(b) contacting the antigen-presenting cell with a test compound; and
(c) detecting IL-10 and IL-12 produced by the antigen-producing cell, wherein induction of IL-12 without a cognate induction of IL-10 by the test compound indicates that the test compound is a candidate compound. Once candidate compounds are identified, they can be subject to further tests to determine their efficacy in inhibiting immune tolerance.

The methods and compositions of the invention described herein may be combined with any other treatment or therapy for treating cancer, for example, chemotherapy, radiation therapy, surgery, and combinations thereof.

EXAMPLES

In the examples below, the following abbreviations have the following meanings. Abbreviations not defined have their generally accepted meanings.

| | |
|---|---|
| ° C. = | degree Celsius |
| μg = | microgram |
| μl = | microliter |
| μM = | micromolar |
| APC = | antigen-presenting cell |
| ELISA = | enzyme linked immunosorbent assay |
| GAPDH = | glyceraldehyde-3-phosphate dehydrogenase |
| HA = | influenza hemagglutinin |
| HBSS = | Hank's Balanced Salt Solution |
| hr = | hour |
| IFN = | interferon |
| LPS = | lipopolysaccharide |
| M = | molar |
| MAP kinase = | mitogen-activated protein kinase |
| mg = | milligram |
| MHC = | major histocompatibility complex |
| min = | minute |
| ml = | milliliter |
| mM = | millimolar |
| mol = | mole |
| PAMP = | pathogen associated molecular pattern |
| PCR = | polymerase chain reaction |
| PEM = | peritoneal elicited macrophage |
| pmol = | picomole |
| RIA = | radioimmunoassay |
| RT PCR = | reverse transcription polymerase chain reaction |
| sec or s = | second |
| TLR = | toll-like receptor |

Materials and Methods

Mice

Male BALB/c mice (6- to 8-weeks old) were obtained from the National Institutes of Health (Frederick, Md.). T-cell receptor (TCR) transgenic mice expressing a T-cell receptor specific for amino acids 110 to 120 from influenza hemagglutinin (HA) presented by I-Ed were a generous gift of H. von Boehmer (Harvard University). Transgenic mice used in these experiments were heterozygous for the transgene. All experiments involving the use of mice were performed in accordance with protocols approved by the Animal Care and Use Committee of the University of South Florida College of Medicine.

Isolation of Peritoneal Elicited Macrophages (PEMs)

BALB/c mice were injected intraperitoneally with 1 mL thioglycollate (DIFCO Laboratories, Detroit, Mich.). Four days later, PEMs were obtained by peritoneal lavage as previously described (Cheng F et al., A critical role for Stat3 signaling in immune tolerance, Inmunity 2003 September; 19(3):425-436).

$1 \times 10^5$ PEMs were plated in triplicate in 96 well plates and treated for 24 hours by the desired test reagent unless otherwise specified. Supernatants were harvested and kept at −70° C. until sandwich ELISA for IL-10 or IL-12p40/70 was performed following manufacturer's instructions (Pharmingen)

Adoptive Transfer

Single cell suspensions were made from the peripheral lymph nodes and spleen collected from TCR transgenic donors. The percentage of lymphocytes double positive for CD4 and the clonotypic TCR in the suspensions was determined by flow cytommetry. Cells were washed three times in sterile Hanks balanced salt solution (HBSS), and injected into the tail vein of male recipients such that a total of $2.5 \times 10^6$ CD4$^+$ anti-HA TCR$^+$ T cells were transferred to each recipient High Dose Peptide Tolerance Model In brief, $2.5 \times 10^6$ anti-HA/1-Ed TCR$^+$ transgenic T cells were transferred into BALB/c mice. One day later, the mice were injected i.v. with a tolerogenic dose of HA-peptide 110-120 (200 μg) in combination with 10 μg of flagellin prepared as described herein (except that the control mice received no flagellin). Two weeks later the animals were sacrificed and the splenocytes harvested. Transgenic T cells numbers in the spleen were assessed by Flow Cytometry with FITC-conjugated rat anti mouse CD4 antibodies (Pharmingen) and biotinylated rat anti-clonotypic TCR antibody MAb 6.5 (kindly donated by Dr Hyam Levitsky, John Hopkins University) and analyzed by Flow-Jo software (Treestar Inc). For in vitro restimulation analysis splenocytes were plated in triplicate in a 96 well plate at a final concentration of $1 \times 10^6$ cells per well, in the presence or absence of synthetic HA-peptide 110-120. After 48 hours of stimulation, supernatants were collected and IFNγ production assessed by sandwich ELISA. Values for cells cultured in media alone are usually less than 10% of the values for antigen-stimulated cells. The data were expressed as the amount of cytokine produced by 100 clonotype$^+$ T cells/well.

FliC Expressing Tumor Cells

ATTCAGTGCCGATACCAAGG (SEQ ID NO:2; left primer) and CACGTGTCGGTGAATCAATC (SEQ ID NO:3; right primer) oligos were designed to amplify the whole fiG coding sequence from *Salmonella typliimurium* (Genbank accession number D13689). The PCR product was identified as a unique band running at the expected size of 16 Kb and purified from the agarose gel using the QIAQUICK gel extraction kit (a reagent kit for extracting DNA from a gel) (Qiagen). The PCR product obtained was initially cloned into the pCR 2.1 vector (Invitrogen TA cloning kit). The proper orientation of the insert was verified by sequencing using an oligo for the T7 promoter present in the plasmid. Following this step, the construct was digested with the restriction enzymes XhoI and HindIII and subcloned into the pcDNA 3.1 (−)Hygro vector (Invitrogen) for IL-10 protein expression in mammalian cells. The inserted fragment was sequenced and identified as the fiG gene of *Salmonella typhimurim*.

The pcDNA 3.1/fliC construct was then used to transfect the murine melanoma cell line B78H1 and the human leukemia cell line K562 using the Lipofectamine plus reagent (Gibco). Transfected cells were initially selected in complete media plus 400 μg/ml of Hygromicin. Cells that survived were further selected in media containing 1200 μg/ml of Hygromicin. Flagellin expression by these cells was confirmed by western blot analysis of cell lysates using an anti-flagellin specific monoclonal antibody (Igen International).

Real Time RT-PCR Analysis

Total RNA was extracted using TRIZOL® reagent (reagent used for RNA extraction from cells and tissues) (Qiagen) and cDNA obtained with the ISCRIPT cDNA synthesis kit (a reagent kit used to obtain cDNA from RNA) (Bio-Rad). Target mRNA was quantified using MYIQ single color real time PCR detection system (a system used for real time PCR) (Bio-Rad) and iQ SYBR green Supermix (a reagent kit used for real time PCR (BioRad). Appropriate primer pairs for IL-12p35, IL-12p40, IL-10, TLR5 and glyceraldehyde-3-phosphate dehydrogenase (GAPDH) were used for PCR amplification (cycling parameters 3 mm 95° C., 15 secs 95 0C, 30 secs 60° C., 40 reps, 1 min 95° C.). Single product amplification was confirmed by melting curve analysis and primer efficiency was near to 100% in all of them. Quantification was expressed in arbitrary units and target mRNA levels were normalized to GAPDH expression.

TLR Ligands

Salmonella typhimurium flagellin preparation was performed as previously described (Ibrahim G F et al., Method for the isolation of highly purified Salmonella flagellins, J Clin Microbiol. 1985 December; 22(6): 1040-1044). Protein purity was verified by Coomasie staining, and its identity was verified by western blot with anti-flagellin monoclonal antibody (Igen international). Endotoxin removal was accomplished by a combination of Detoxi-Gel AffinityPak columns (Pierce) and filtration through 100 Kd pore size centricon columns (Millipore). Endotoxin removal was confirmed using the Limulus Amebocyte Lysate test (Cambrex). In addition, the most relevant experiments were repeated using commercially available S. typhimurium flagellin (InVivoGen), which resulted in essentially identical results.

LPS (Sigma) and CpG (InVivoGen Catalog No. ODN1826) were also used as indicated.

Serum Analysis

Mice were treated with flagellin or LPS (30 μg) by tail vein injection. After 90 minutes of treatment, the animals were sacrificed and blood obtained by heart puncture. The blood was centrifuged at 13K rpm and 4° C., and the resultant serum was subject to cytokine analysis by sandwich ELISA as described above.

RAW 264.7 Transfection

RAW 264.7 cells were transfected with a plasmid expressing the murine TLR5 gene (pUNO-mTLR5-HA from InVivoGen) using Lipofectamine Plus reagent (Gibco).

The transfected cells were selected with media suplemented with 1 μg/ml Blasticidin S and expression of the target gene was verified by real time RT-PCR as described above.

Example 1

Flagellin as an Adjuvant

Figure 1:
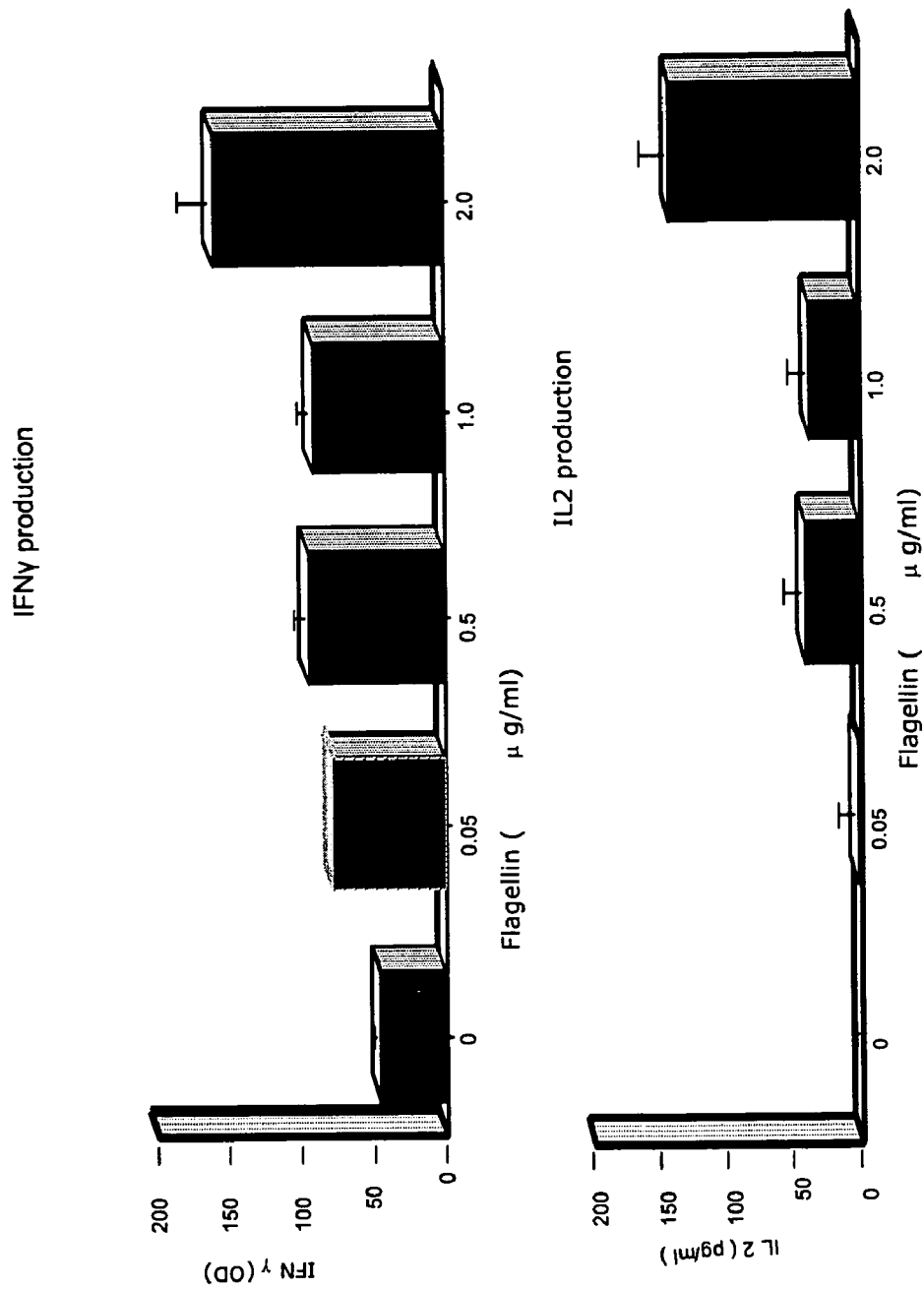
FIG. 1. Flagellin treatment enhances IL-2 and IFNγ production by antigen specific CD4+ T cells in a dose dependent manner.

We hypothesized that flagellin can provide a "danger" signal to activate APCs in tumor antigen presentation, thereby inhibiting T cell tolerance to the tumor antigen. To this end, we first evaluated the adjuvant function of our flagelllin preparation as described in Materials and Methods. As shown in FIG. 1, splenocytes treated with different concentrations of flagellin were able to efficiently present an antigen to $CD4^+$ T cells. In this case the model antigen, influenza hemagglutinin (HA) peptide, was presented to HA specific transgenic T cells, and T cell activation was demonstrated by an increase in the production of IFNγ and IL-2. Thus, flagellin can be used as an adjuvant.

Example 2

Flagellin Inhibits Tolerance

Next we determined whether in vivo treatment with flagellin could prevent antigen specific T cell tolerance induced by high doses of antigens. HA specific $CD4^+$ T cells were transferred to a normal syngeneic animal, and the host was immunized with a recombinant vaccinia virus containing the HA antigen sequence in its genome. The T cell response was quantified by in vivo clonal expansion (analyzed by flow cytometry), and by the in vitro production of cytokines by HA-T cells isolated from the host and plated together with APCs plus the antigen.

Figure 2:
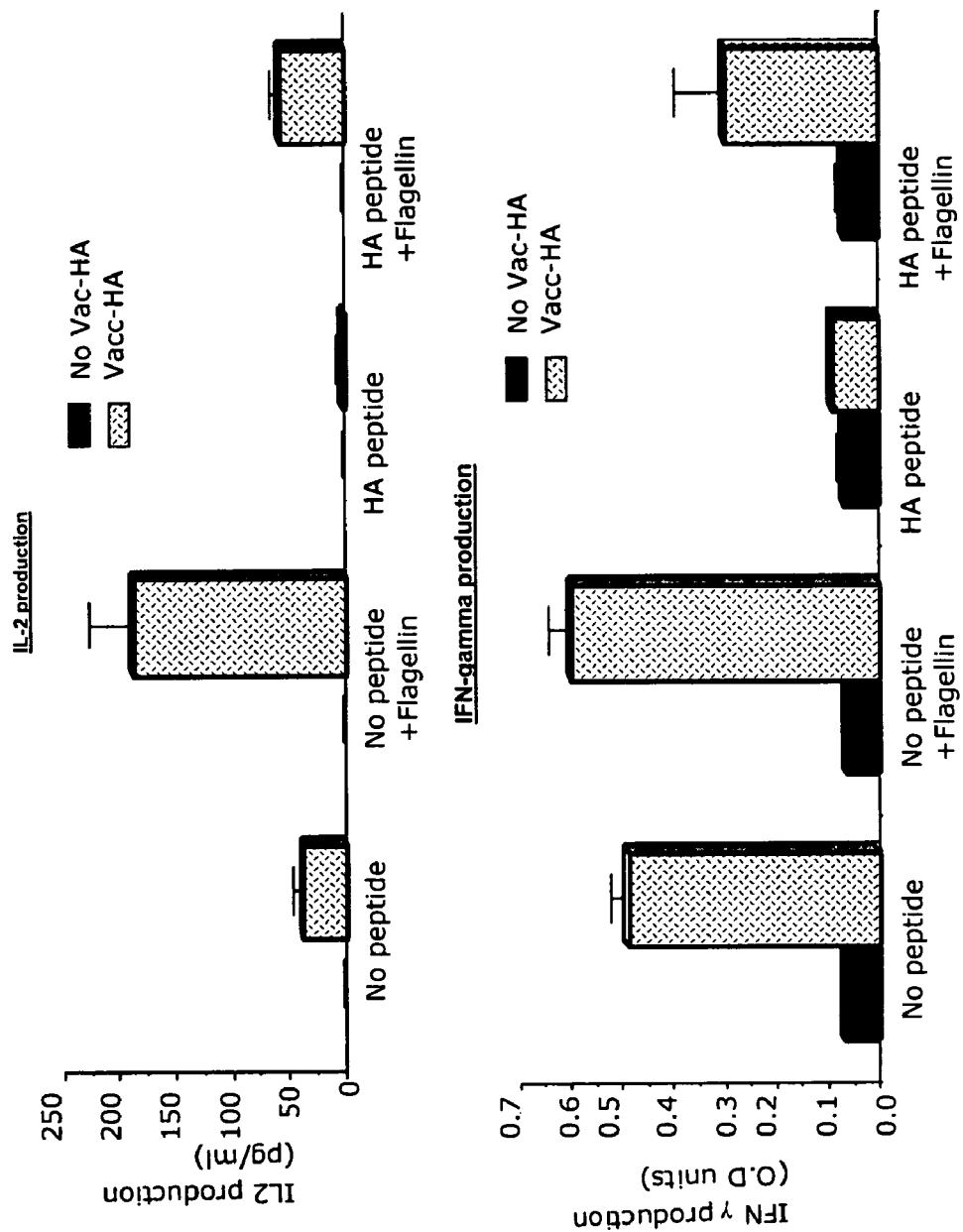
FIG. 2. Flagellin prevents tolerance. No Vac-HA: the host animal was not immunized with a recombinant vaccinia virus engineered to include the influenza hemagglutinin (HA) antigen sequence in its genome. Vacc-HA: the host animal was immunized with such vaccinia virus. The treatment under the columns (No peptide, No peptide+Flagellin, HA peptide, and HA peptide+flagellin) indicates the presence or absence of a tolerogenic dose of HA peptide (275 μg) and flagellin (10 μg).

The results show that the production of cytokines (FIG. 2) and clonal expansion were almost completely abrogated in the animals treated with a tolerogenic dose of the antigen, HA peptide. In contrast, the mice injected with the same dose of HA peptide as well as flagellin (HA peptide plus flagellin) still produced significant levels of IL-2 and IFNγ. These results indicate that flagellin has preserved the capacity of the $CD4^+$ T cells to respond to tolerogenic levels of antigens.

Example 3

Flagellin Induces Costimulatory Molecules

To further characterize the phenotype of APCs treated in vitro with flagellin, we examined other surface molecules of APCs. The results indicate that peritoneal macrophages treated with flagellin displayed higher levels of B7.1, CD40 and MHC class I molecules as compared with untreated macrophages (data not shown).

Example 4

Flagellin Induces IL-12 but not IL-10

It is plausible therefore that APCs presenting antigens in the context of flagellin stimulation provide more adequate costimulation to $CD4^+$ T cells, which in turn is responsible for switching a tolerogenic response to a priming event. Other factor that may play a role in determining the outcome of the APC-T cell interaction is the nature of the cytokines present in the environment at the time of antigen presentation. Anti-inflammatory cytokines like IL-10 will influence the T cell decision toward an anergy response. Inflammatory cytokines such as IL-12 play the opposite role, inducing T cell differentiation into a helper T cell that will drive an adaptive immune response against the antigen presented by the APC.

Figure 3:
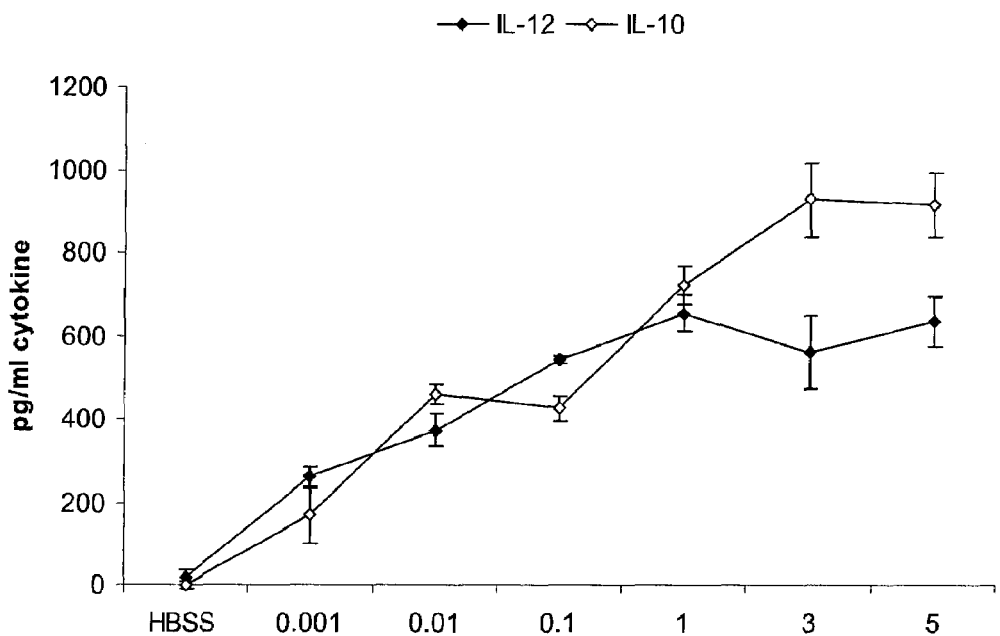
FIG. 3. IL-12, but not IL-10, was detected in the supernatants of flagellin stimulated peritoneal elicited macrophage (PEM).
Figure 3:
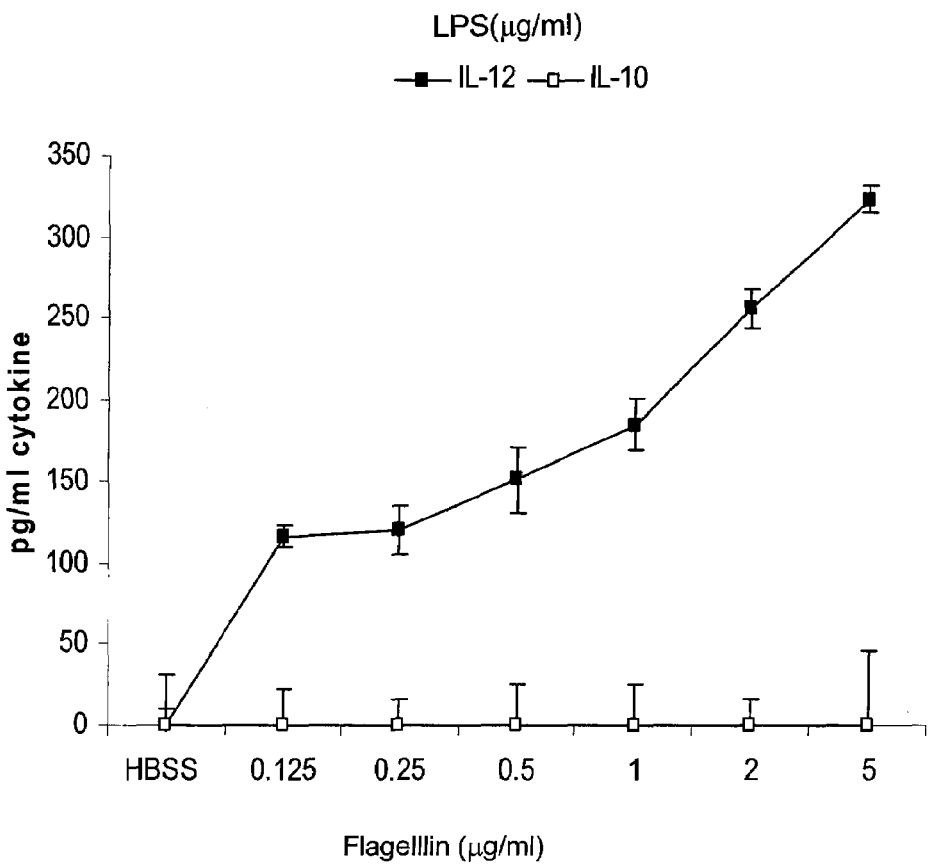
Figure 3:
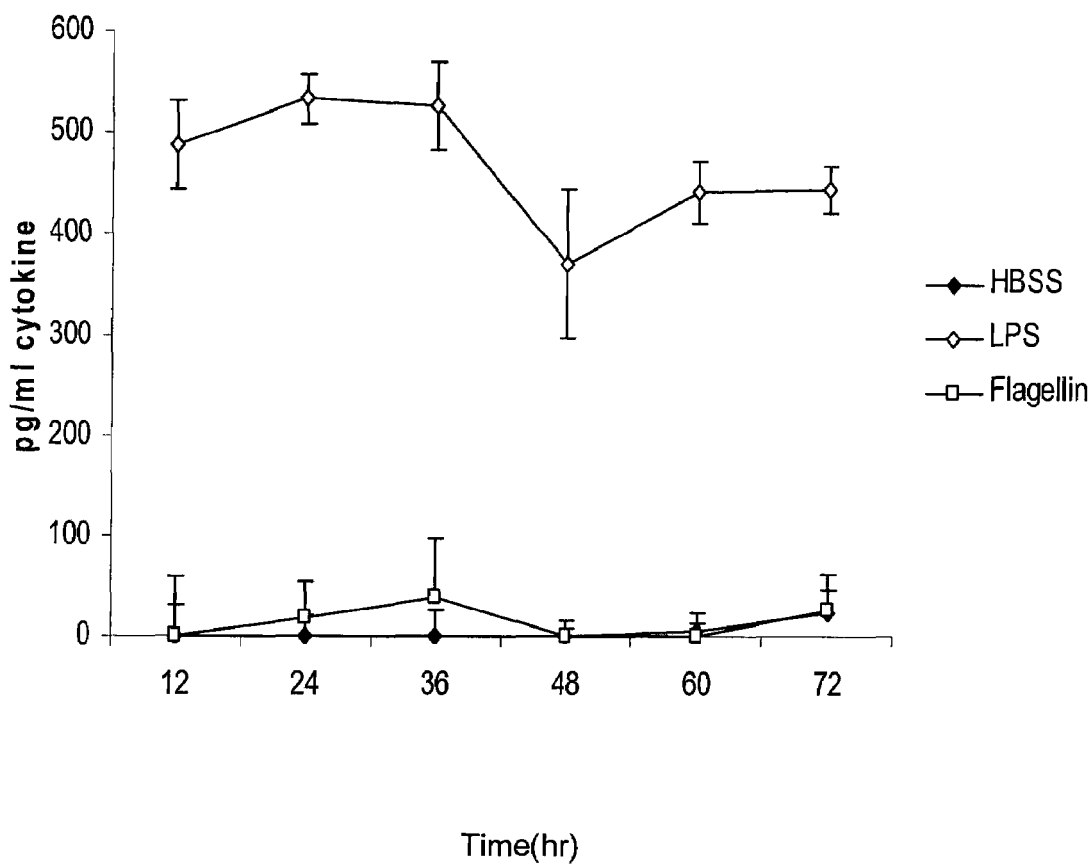

We treated peritoneal macrophages for 24 hours with various concentrations of flagellin or LPS and the supernatants analyzed by ELISA to detect the presence of IL-12p40/70 and IL-10. Interestingly, as shown in FIG. 3, macrophages stimulated with flagellin predominantly produced IL-12, while the macrophages stimulated with LPS produced both IL-10 and IL-12. This preferential induction of IL-12 in response to flagellin can explain the ability of these APCs to prevent tolerance induction. It also indicates a difference on downstream signaling pathways triggered by LPS (TLR4 signaling) and flagellin (TLR5 signaling).

Example 5

Flagellin Depends on TLR5 to Induce IL-12

To determine if TLR5 is required for flagellin-induced IL-12 production, we transfected the murine macrophage cell line RAW 264.7 with a construct encoding murine TLR5. Both the wild-type and transfected RAW 264.7 cells were treated with flagellin, and the level of IL-12 expression was measured by real time RT PCR. As shown in FIG. 4, the wild-type RAW 264.7 did not express any IL-12 when simulated with flagellin, while LPS induced strong IL-12 expression. The TLR5-transfected RAW 264.7, however, responded to flagellin and produced IL-12. Therefore, flagellin-induced IL-12 production is dependent on the presence of TLR5.

Example 6

Time Course of IL-12 Induction

To study the time course of IL-10 and IL-12 production, PEMs were stimulated with flagellin (5 µg/ml), LPS (1 µg/ml) or CpG (2 µM) for the indicated periods of time. The cells were then harvested in TRIZOL® and RNA extracted. The results (FIG. 5) show that all three TLR ligands induced IL-12 in similar temporal patterns. In contrast, flagellin only induced IL-10 transiently and weakly, while LPS and CpG led to strong IL-10 expression for a long time.

Example 7

Flagellin Inhibits LPS or CpG-Induced IL-10 Production

As shown above, flagellin alone induces little, if any, IL-10 production. We further discovered that flagellin can inhibit LPS- or CpG-induced IL-10 production. In these experiments, PEM were treated with LPS (1 µg/ml) or CpG (2 µM) in the presence of absence of flagellin (20 µg/ml) for various periods of time. The cells were harvested and IL-10 mRNA was detected. The results show that IL-10 mRNA levels were lower when flagellin was present (FIG. 6A). IL-10 protein production was also inhibited by flagellin (FIG. 6B). The inhibitory effect of flagellin is dependent on the presence of TLR5, as flagellin had no effect in RAW 264.7 cells, which do not express TLR5 (FIG. 6B).

The inhibitory effect of flagellin depends on when it is added. PEM were stimulated with 5 µg/ml flagellin for 0, 3, 6 or 12 hours, and afterwards LPS was added to the media (final concentration 1 µg/ml). After 2 hours of LPS stimulation, the cells were harvested and RNA analyzed as described above. FIG. 7A shows that the inhibitory effect of flagellin increased with length of pre-incubation. The dynamics of LPS-induced IL-10 or IL-12 induction, however, was not dramatically changed by flagellin pre-incubation (FIGS. 7B, 7C).

Example 8

In Vivo Effect of Flagellin

To test the effect of flagellin in vivo, BALB/c mice were injected i.v. with 30 µg of flagellin or LPS. The serum level of IL-12 and IL-10 were determined 1.5 hours later. Consistent with the results in vitro, LPS induced strong production of both IL-12 and IL-10, while flagellin induced IL-12 only (FIG. 8A).

The effect of flagellin on tolerance was also tested. A tolerogenic dose of HA peptide (200 µg) with or without 10 µg of flagellin was given to animals that had received 6.5 T cell transfer (T cells that are specific for HA peptide) for one day. The animals were sacrificed and splenocytes harvested one Day+15 after adoptive transfer. FIG. 8B shows that percentage of clonotypic 6.5 T cells in the spleens of the animals treated with HA only was reduced by two thirds compared to control. In contrast, the percentage of these T cells were almost normal in the animals treated with HA and flagellin. Thus, flagellin can inhibit tolerance both in vivo and in vitro. Similarly, upon in vitro restimulation with HA peptide for 48 hours, splenocytes from animals injected with a tolerogenic dose of HA peptide plus flagellin produced significant levels of IFN gamma, indicating that they have been primed against HA (FIG. 8C). On the contrary, splenocytes from animals that received the antigen without flagellin produced IFN-gamma at equal or even lower levels than the cells that have never been exposed to the antigen, indicating that the animals receiving HA antigen alone have been tolerized to the antigen.

In summary, these results indicate that flagellin can induce IL-12 production in vivo without inducing IL-10. Flagellin also inhibits tolerance in vivo as well as in vitro.

Example 9

The Effect of Flagellin-Expressing B78-H1 Cells

To deliver flagellin to a subject for the purpose of inhibiting tolerance and enhancing immune responses against an antigen, it is desirable to use a flagellin-expressing cell, because such cells can release flagellin for a period of time to continuously stimulate the immune system. Toward this end, we constructed a flagellin-expressing cell using the murine melanoma cell line B78-H1. The cells were kindly provided by Dr. H. Levistky (John Hopkins University). This cell line does not express MHC class I antigens or class II molecules (Levitsky H I et al., In vivo priming of two distinct antitumor effector populations: the role of MHC class I expression, J Exp Med 1994 Apr. 1; 179(4):1215-24), so it does not raise strong alloresponses against the MHC class molecules. A strong alloresponse would divert the immune system from the antigens of therapeutic interest, and it may also rapidly eliminate the flagellin-expressing cell from the subject.

We transfected B78-H1 cells with a construct expressing the fliC gene from *S. typhimurium* as described above. The cell lysates from this cell stimulated IL-12 production by PEM more than twice as effectively as the wild-type, untransfected cell (FIG. 9). Therefore, the cell can be successfully used to deliver functional flagellin.

A number of embodiments of the invention have been described. Nevertheless, it will be understood that various modifications may be made without departing from the spirit and scope of the invention.

All of the publications cited in this application, including patents, patent applications, Genbank sequence and information, and other publications, are herein incorporated by reference in their entirety to the same extent as if the disclosure of each individual publication was specifically and individually indicated to be incorporated by reference in its entirety.

What is claimed is:

1. A composition comprising a flagellin-expressing eukaryotic cell, wherein the cell has been lethally irradiated.

2. The composition of claim 1 wherein the flagellin-expressing cell is a mammalian or avian cell.

3. The composition of claim 1 wherein the flagellin-expressing cell lacks MHC class I molecules, MHC class II molecules, or both.

4. The composition of claim 1 wherein the flagellin-expressing cell is a B78-H1 cell or K562 cell that has been transfected with a flagellin gene.

5. The composition of claim 1 wherein the flagellin-expressing cell expresses a flagellin of *Escherichia, Salmonella, Proteus, Pseudomonas, Bacillus, Campylobacter, Vibrio, Treponema, Legionella, Clostridia*, or *Caulobacter* spp.

6. The composition of claim 1, further comprising an antigen that is associated with a tumor cell.

7. The composition of claim 6 wherein the tumor cell is a cell from a tumor selected from the group consisting of leukemia, lymphoma, lung cancer, prostate cancer, colorectal cancer, thyroid cancer, renal cancer, adrenal cancer, liver cancer, pancreatic cancer, breast cancer, and central and peripheral nervous system cancer.

8. The composition of claim 6 wherein the antigen is a tumor cell that has been lethally irradiated.

9. The composition of claim 6 wherein the flagellin-expressing cell and the tumor cell are from the same species.

10. The composition of claim 9 wherein the species is human.

11. The composition of claim 6 wherein the flagellin-expressing cell and the tumor cell are derived from the same individual.

12. A method for preparing an adjuvant, comprising lethally irradiating a flagellin-expressing eukaryotic cell.

13. The method of claim 12, wherein the flagellin-expressing cell is a mammalian or avian cell.

14. The method of claim 12, wherein the flagellin-expressing cell lacks MHC class I molecules, MHC class II molecules, or both.

15. The method of claim 12, wherein the flagellin-expressing cell is a B78-H1cell or K562 cell that has been transfected with a flagellin gene.

16. The method of claim 12, wherein the flagellin-expressing cell expresses a flagellin of *Escherichia, Salmonella, Proteus, Pseudomonas, Bacillus, Campylobacter, Vibrio, Treponema, Legionella, Clostridia*, or *Caulobacter* spp.

17. A method for inducing the production of IL-12 in a subject, comprising administering to the subject a flagellin-expressing eukaryotic cell, wherein the cell has been lethally irradiated.

18. The method of claim 17, wherein the flagellin-expressing cell is a mammalian or avian cell.

19. The method of claim 17, wherein the flagellin-expressing cell lacks MHC class I molecules, MHC class II molecules, or both.

20. The method of claim 17, wherein the flagellin-expressing cell is a B78-H1 cell or K562 cell that has been transfected with a flagellin gene.

21. The method of claim 17, wherein the flagellin-expressing cell expresses a flagellin of *Escherichia, Salmonella, Proteus, Pseudomonas, Bacillus, Campylobacter, Vibrio, Treponema, Legionella, Clostridia*, or *Caulobacter* spp.

* * * * *

SEQUENCE LISTING

<160> NUMBER OF SEQ ID NOS: 3

<210> SEQ ID NO 1
<211> LENGTH: 4

-continued

```
<212> TYPE: PRT
<213> ORGANISM: Artificial Sequence
<220> FEATURE:
<223> OTHER INFORMATION: flagellin motif
<220> FEATURE:
<221> NAME/KEY: VARIANT
<222> LOCATION: (2)...(3)
<223> OTHER INFORMATION: Xaa = any amino acid.
<220> FEATURE:
<221> NAME/KEY: VARIANT
<222> LOCATION: 4
<223> OTHER INFORMATION: Xaa = amino acid with a bulky hydrophobic side
      chain.

<400> SEQUENCE: 1

Tyr Xaa Xaa Xaa
 1

<210> SEQ ID NO 2
<211> LENGTH: 20
<212> TYPE: DNA
<213> ORGANISM: Artificial Sequence
<220> FEATURE:
<223> OTHER INFORMATION: oligo designed to amplify the whole fliC coding
      sequence from Salmonella typhimurium

<400> SEQUENCE: 2
attcagtgcc gataccaagg                                               20

<210> SEQ ID NO 3
<211> LENGTH: 20
<212> TYPE: DNA
<213> ORGANISM: Artificial Sequence
<220> FEATURE:
<223> OTHER INFORMATION: oligo designed to amplify the whole fliC coding
      sequence from Salmonella typhimurium

<400> SEQUENCE: 3
cacgtgtcgg tgaatcaatc                                               20
```